US00PP31386P2

(12) United States Plant Patent
Lommerse

(10) Patent No.: US PP31,386 P2
(45) Date of Patent: Jan. 21, 2020

(54) ***LEWISIA* PLANT NAMED 'LORE3509'**

(50) Latin Name: *Lewisia cotyledon*
Varietal Denomination: LORE3509

(71) Applicant: Lommerse Holding BV, Mariahout (NL)

(72) Inventor: Henry Lommerse, Mariahout (NL)

(73) Assignee: Lommerse Holding BV, Mariahout (NL)

( * ) Notice: Subject to any disclaimer, the term of this patent is extended or adjusted under 35 U.S.C. 154(b) by 0 days.

(21) Appl. No.: 16/350,123

(22) Filed: Sep. 27, 2018

(51) Int. Cl.
*A01H 6/30* (2018.01)
*A01H 5/02* (2018.01)

(52) U.S. Cl.
USPC ..... Plt./263.1

(58) Field of Classification Search
USPC ..... Plt./263.1
CPC ..... A01H 6/30; A01H 6/00; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Lewisia* plant named 'LORE3509' which is characterized by improved plant vigor, an abundance of dark greyed-green foliage which is arranged in a symmetrical rosette, vibrant red-purple flowers, recurrent flowering from spring through summer with no vernalization requirement, as well as the stability of these characteristics from generation to generation.

3 Drawing Sheets

Latin name of the genus and species: The Latin name of the genus and species of the novel variety disclosed herein is *Lewisia cotyledon.*

Variety denomination: The inventive variety of *Lewisia* disclosed herein has been given the variety denomination 'LORE3509'.

BACKGROUND OF THE INVENTION

Parentage: 'LORE3509' is a seedling selection resulting from the controlled self-pollination of *Lewisia cotyledon* '103500/A' (not patented), a variety developed and owned by the inventor. The crossing was made by the inventor in April of 2011 at a plant breeding facility in Mariahout, the Netherlands. In the summer of 2014, one seedling was observed which exhibited unique growth and flower characteristics. The seedling was isolated for further evaluation in order to confirm the distinctness and stability of the characteristics first observed. Upon confirmation of distinctness and stability, 'LORE3509' was selected for commercialization in May of 2012.

Asexual Reproduction: Asexual reproduction of the new cultivar 'LORE3509', by way of meristematic tissue culture, was first initiated in June of 2012 at a laboratory in Rijswijk, The Netherlands. Through five subsequent generations, the unique features of this cultivar have proven to be stable and true to type.

SUMMARY OF THE INVENTION

The cultivar 'LORE3509' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LORE3509'. These characteristics in combination distinguish 'LORE3509' as a new and distinct *Lewisia* cultivar:

1. 'LORE3509' exhibits improved plant vigor; and
2. 'LORE3509' exhibits an abundance of dark greyed-green foliage, arranged in a symmetrical rosette; and
3. 'LORE3509' exhibits vibrant red-purple flowers, when fully opened; and
4. 'LORE3509' exhibits recurrent flowering from spring through summer; and
5. 'LORE3509' does not require vernalization for flowering.

BOTANICAL DESCRIPTION OF THE PLANT

Figure 1:
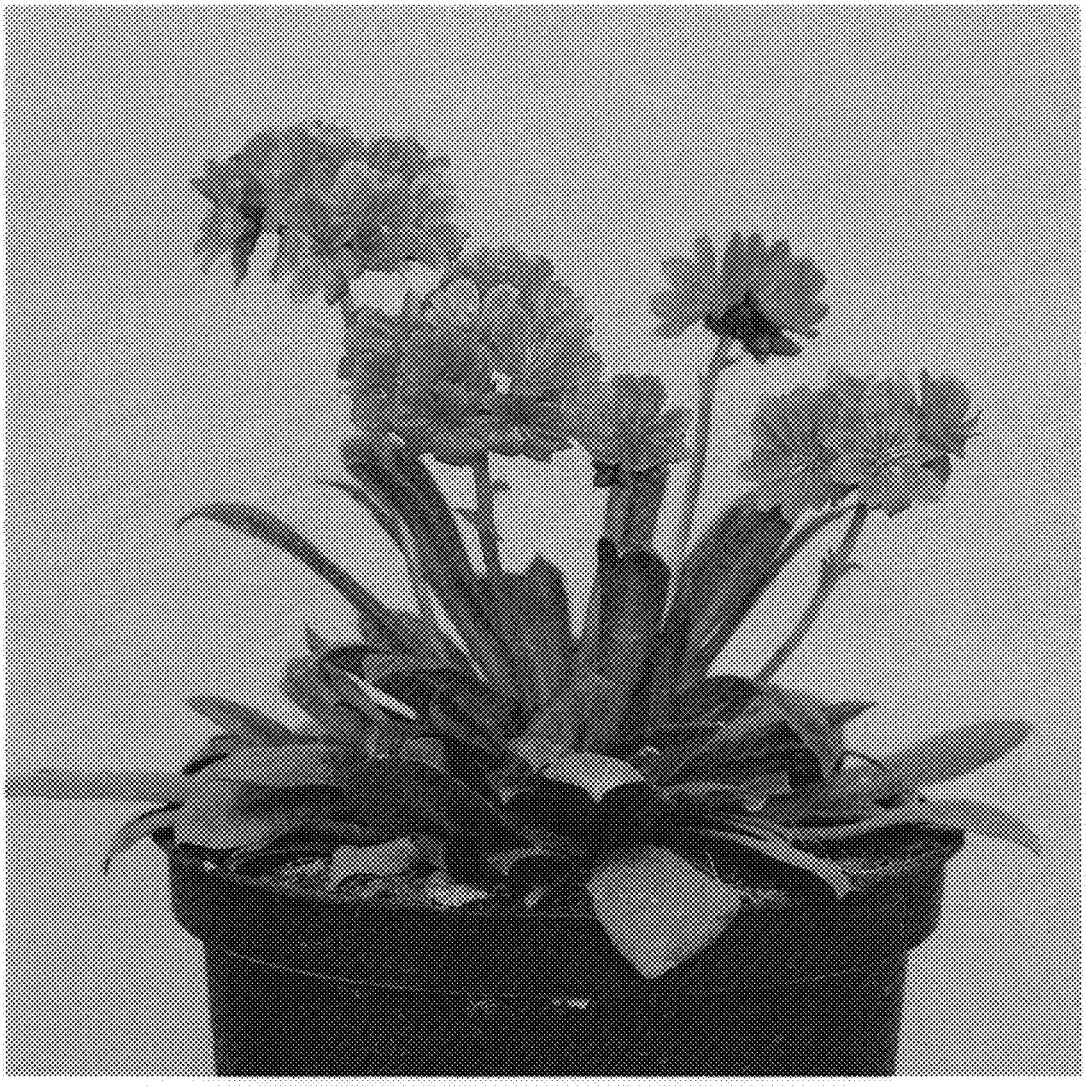
FIG. 1 illustrates, as nearly true as it is reasonably possible to make the same in color photographs of this type, an exemplary plant of 'LORE3509' in flower, grown in a greenhouse in Mariahout, The Netherlands. This plant is approximately 12 months old, shown planted in a 15 cm container.
Figure 2:
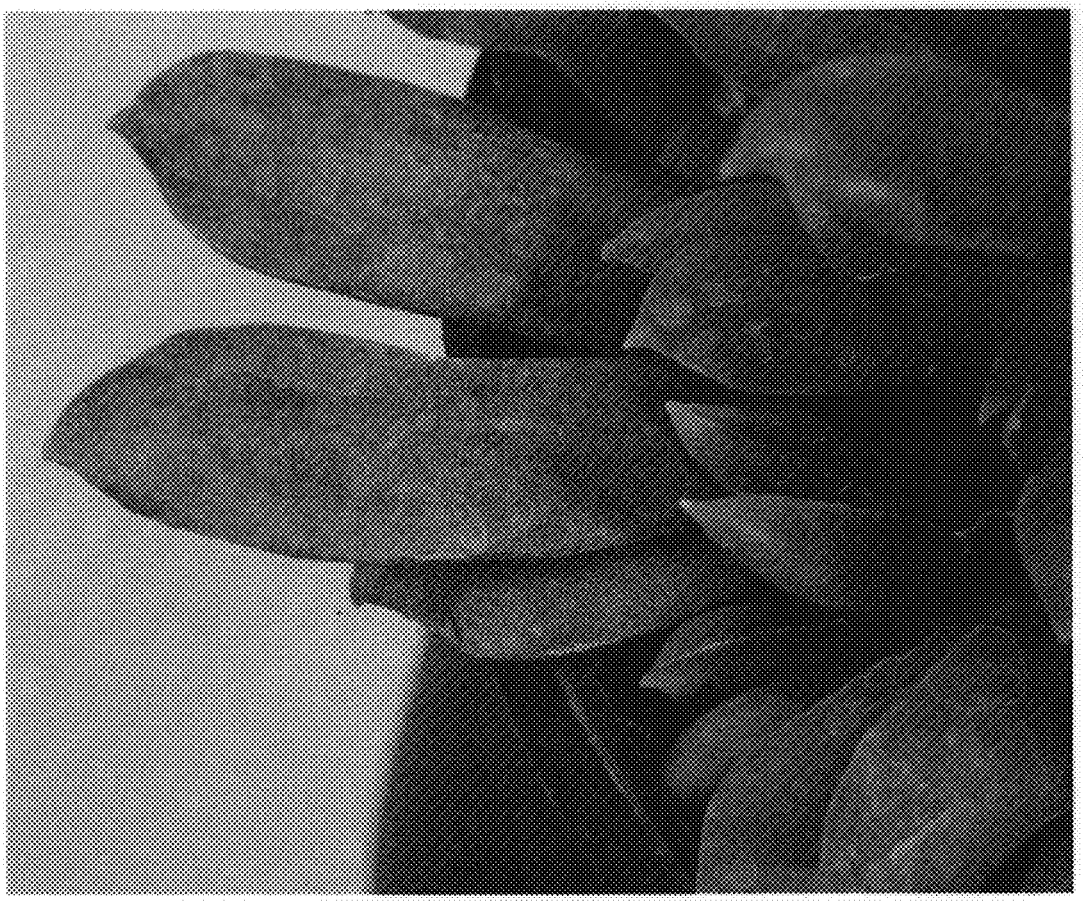
FIG. 2 illustrates, as nearly true as it is reasonably possible to make the same in color photographs of this type, the typical foliage of 'LORE3509'.
Figure 3:
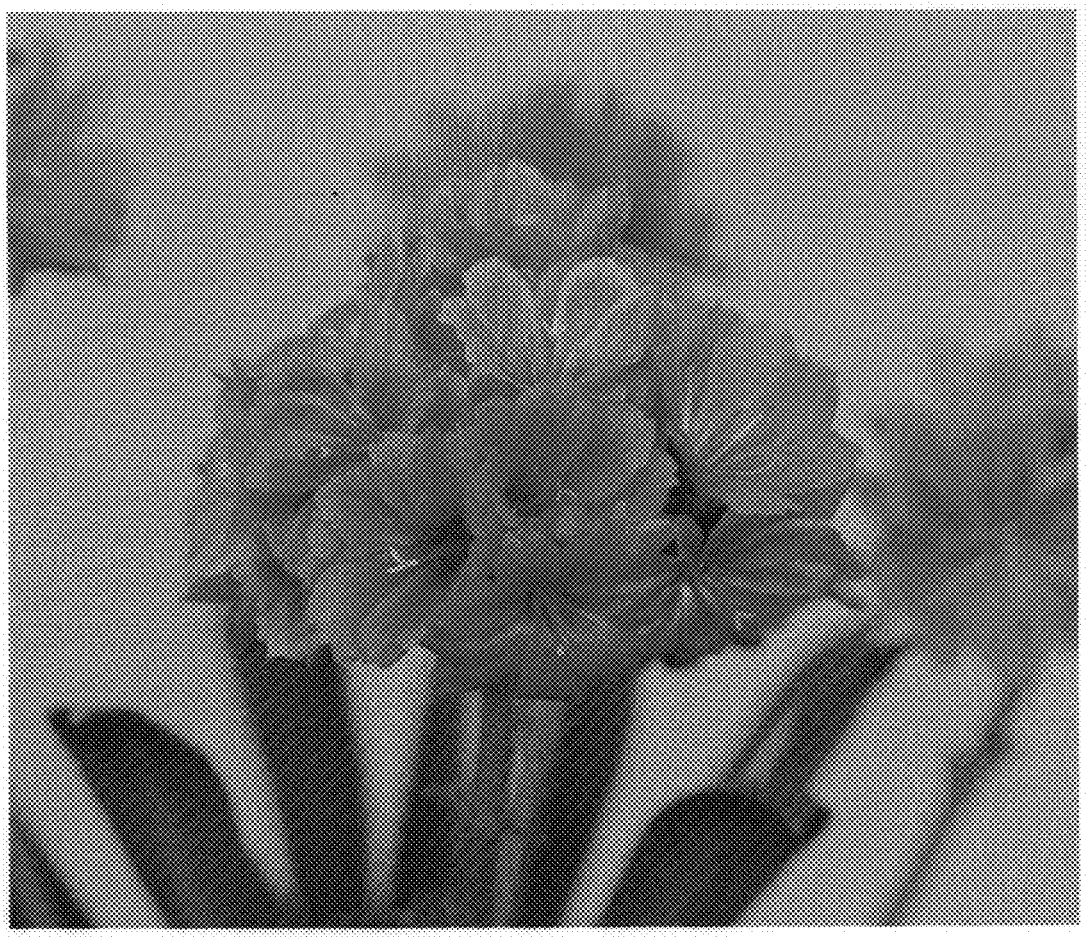
FIG. 3 illustrates, as nearly true as it is reasonably possible to make the same in color photographs of this type, the typical inflorescence of 'LORE3509'.

The following observations and measurements made in February of 2018 describe averages from a sample set of six specimens of 12 month old 'LORE3509' plants grown in 15 cm nursery containers at a commercial greenhouse in Mariahout, the Netherlands. Plants were produced under full sun exposure, with minimal subsurface irrigation, no fertilizer application, and no chemical pest and disease control measures. No photoperiodic treatments or artificial light was given to the plants.

Those skilled in the art will appreciate that certain characteristics will vary with older or, conversely, with younger plants. 'LORE3509' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'LORE3509' and comparisons with the parent plants and closest known comparator are provided below.

Plant description:

*Growth habit*.—Herbaceous evergreen perennial with foliage growing in a non-branched basal rosette.

*Plant shape*.—Flattened globular with inflorescence carried above the foliar plane.

*Height from soil level to top of foliar plane*.—9.1 cm.

*Height from soil level to top of floral plane*.—14.4 cm.

*Plant spread*.—Average of 20.2 cm.

*Growth rate*.—Moderate.

*Plant vigor*.—Moderate.

*Propagation*.—Type — Meristematic tissue culture. Time to initiate rooting — Approximately 21 days at 18 degrees Celsius. Crop time — Approximately 14 weeks to produce a mature rooted cutting.

*Disease and pest resistance or susceptibility*.—Neither resistance nor susceptibility to typical *Lewisia* pests and diseases has been observed.

*Environmental tolerances*.—Adapt to USDA Zones 7 to 10 and temperatures as high as 40 degrees Celsius and at least as low as negative 12 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosulate.

*Division*.—Simple.

*Attachment*.—Sessile.

*Quantity*.—Approximately 146 leaves per rosette.

*Shape*.—Narrowly oblanceolate.

*Dimensions*.—9.7 cm long, 2.2 cm wide, and 0.2 cm thick, on average.

*Aspect*.—Slightly to moderately convex; slightly curved downward at the apex at an angle of 70 degrees to the lamina.

*Attitude*.—Younger foliage near the center of the rosette is very upright; foliage becoming progressively more relaxed towards the outer whorl of the rosette yet still generally upright; average angle of 50 degrees from horizontal.

*Apex*.—Apiculate.

*Base*.—Long cuneate.

*Margin*.—Entire; not undulated or lobed.

*Pubescence, texture and luster of the adaxial surface*.—Glabrous, moderately leathery, and matte.

*Pubescence, texture and luster of the abaxial surface*.—Glabrous, moderately leathery, and matte.

*Color*.—Juvenile foliage, adaxial surface — Green, nearest to RHS 143A. Juvenile foliage, abaxial surface — Yellow-green, nearest to in between RHS 144B and 145A. Mature foliage, adaxial surface — Yellow-green, nearest to RHS 147A, and fading to a lighter shade of green-yellow towards the base, nearest to RHS 145A. Mature foliage, abaxial surface — Yellow-green, nearest to RHS 146B, and fading to a lighter shade of green-yellow towards the base, nearest to RHS 146C.

*Venation*.—Venation — No veins are visible, except the main central vein on the abaxial surface. Color, adaxial surface — No veins are visible. Color, abaxial surface — Midrib is yellow-green, nearest to RHS 145B.

*Petiole*.—No petiole; leaves are sessile.

Inflorescence:

*Type*.—Axillary cyme.

*Natural flowering season*.—Spring and summer.

*Bloom habit*.—Recurrent flowering, approximately every 10 weeks.

*Flowers per inflorescence*.—Average of 35.

*Flowers per plant*.—Approximately 180 open flowers and 60 flower buds.

*Inflorescence height*.—Approximately 3.4 cm (measured from base of lowest flower to top of upper flower).

*Inflorescence diameter*.—Approximately 5.9 cm.

*Peduncle*.—Attitude — Upright and outward. Cross section — Ovoid; somewhat flattened. Dimensions — 9.6 cm long and 0.3 cm wide. Texture — Smooth; glabrous. Luster — Moderately glossy. Strength — Moderately strong. Color — Yellow-green, nearest to RHS 152B.

Flower buds:

*Bud shape*.—Narrow obovate.

*Bud dimensions*.—0.9 cm long and 0.3 cm in diameter.

*Bud texture*.—Smooth; glabrous.

*Bud luster*.—Moderately glossy.

*Bud color*.—Upper surface is orange-red, nearest to RHS N34C; lower surface is yellow-green, nearest to RHS 146B.

Flower:

*Flower shape*.—Rotate, with a single whorl of petals.

*Lastingness*.—Flowers persist for approximately 10 days.

*Persistence*.—Persistent.

*Flower aspect*.—Outward to upright.

*Fragrance*.—Non-fragrant.

*Vertical height*.—Approximately 2.5 cm.

*Diameter*.—Approximately 2.5 cm.

*Depth*.—Approximately 1.3 cm.

*Calyx*.—Calyx shape — Comprised of two oppositely placed sepals. Calyx dimensions — 0.6 cm in diameter at the widest point and 0.4 at the narrowest; 0.6 cm deep. Sepals — Sepal arrangement — Opposite; not fused. Number of sepals — 2. Dimensions — 0.5 cm long and 0.5 cm wide. Margins — Short pectinate; not undulated. Shape — Near orbicular. Apex — Short pectinate. Base — Broad cuneate. Sepal texture (inner surface) — Smooth; glabrous.

Sepal texture (outer surface) — Smooth; glabrous. Sepal luster (inner surface) — Glossy. Sepal luster (outer surface) — Glossy. Sepal color, when opening (inner surface) — Yellow-green, nearest to RHS 146B. Sepal color, when opening (outer surface) — Yellow-green, nearest to RHS 146B. Sepal color, when fully opened (inner surface) — Yellow-green, nearest to RHS 146C. Sepal color, when fully opened (outer surface) — Yellow-green, nearest to RHS 146C.

*Corolla*.—Pedicel — Attitude — At an angle of approximately 30 degrees to the peduncle. Cross section — Ovoid; somewhat flattened. Dimensions — 0.2 cm long and 0.075 cm wide. Texture — Smooth; glabrous. Luster — Moderately glossy. Strength — Moderately strong. Color — Yellow-green, nearest to RHS 146C. Petals — Quantity — 9. Arrangement — Rotate. Fused or free — Free. Dimensions — Approximately 1.5 cm long and 0.6 cm wide. Shape — Obovate. Apex — Undeeply praemorse. Base — Cuneate. Aspect — Lightly involute and moderately reflexed. Margin — Entire; lightly undulated. Texture (upper side) — Glabrous and slightly velvety. Texture (under side) — Glabrous and slightly velvety. Luster (upper side) — Matte. Luster (under side) — Slightly glossy. Color when opening (upper side) — Red, nearest to RHS 45D. Color when opening (under side) — Red, nearest to RHS 42C, and fading to RHS 45D at the base. Color when fully opened (upper side) — Red-purple, nearest to RHS 61B. Color when fully opened (under side) — Red-purple, nearest to in between RHS 61B and 61C. Venation color (upper side) — No veins visible. Venation color (under side) — No veins visible. Color when faded (upper side) — Red-purple, nearest to RHS 72A. Color when faded (under side) — Red-purple, nearest to RHS 72A.

Reproductive organs:

*Androecium*.—Stamen quantity — 8. Filament — Dimensions — 1.0 cm and 0.1 cm in diameter. Color — Purple, nearest to RHS 75B. Anther — Attachment — Basifixed. Shape — Narrow oblong. Dimensions — 0.15 cm long and 0.04 cm in diameter. Color — Orange-red, nearest to RHS N34B. Pollen — Amount of pollen — Moderately abundant. Pollen color — Yellow-orange, RHS 20A.

*Gynoecium*.—Pistil quantity — One. Length overall — 0.7 cm. Stigma — Shape — Trifurcated. Dimensions — Approximately 0.2 cm in diameter and 0.2 cm long. Color — Red-purple, nearest to RHS 67D. Style — Dimensions — 0.5 cm long and 0.1 cm in diameter. Color — Red-purple, nearest to RHS 67C. Ovary — Color — Red-purple, nearest to RHS 67C.

Seed and fruit: Not observed.

COMPARISONS WITH THE PARENT PLANT AND CLOSEST KNOWN COMPARATOR

Plants of the new cultivar 'LORE3509' differ from the parent, *Lewisia cotyledon* '103500/A' (not patented), in the following characteristics described in Table 1 below.

TABLE 1

| Characteristic | 'LORE3509' | '103500/A' |
|---|---|---|
| Growth habit. | Rosette is more symmetrical than that of '103500/A'. | Rosette is less symmetrical than that of 'LORE3509'. |
| Plant height. | Shorter than '103500/A'. | Taller than 'LORE3509'. |
| Bloom period. | Longer than that of '103500/A'. | Shorter than that of 'LORE3509'. |
| General coloration of the flower, when fully open. | Red-purple. | Vibrant pink. |

COMPARISONS WITH THE CLOSEST KNOWN COMPARATOR

Plants of the new cultivar 'LORE3509' differ from the closest known commercial comparator, *Lewisia* 'Sunset Strain' (not patented), in the following characteristics described in Table 2 below.

TABLE 2

| Characteristic | 'LORE3509' | 'Sunset Strain' |
|---|---|---|
| Plant height. | Shorter than 'Sunset Strain'. | Taller than 'LORE3509'. |
| Foliage size. | Smaller than 'Sunset Strain'. | Larger than 'LORE3509'. |
| Growth habit. | Rosette is more symmetrical than that of 'Sunset Strain'. | Rosette is less symmetrical than that of 'LORE3509'. |
| General coloration of the flower, when fully open. | Red-purple. | Orange-yellow. |

That which is claimed is:

1. A new and distinct variety of *Lewisia* plant named 'LORE3509', substantially as described and illustrated herein.

* * * * *